United States Patent [19]

Paust et al.

[11] Patent Number: 5,689,022
[45] Date of Patent: Nov. 18, 1997

[54] PREPARATION OF β-CAROTENE PRODUCTS WITH A HIGH 9 (Z) CONTENT

[75] Inventors: Joachim Paust, Neuhofen; Michael John, Lambsheim, both of Germany

[73] Assignee: BASF Aktiengesellschaft, Ludwigshafen, Germany

[21] Appl. No.: 641,032

[22] Filed: Apr. 30, 1996

[30] Foreign Application Priority Data

May 12, 1995 [DE] Germany ............... 19 517 422.4

[51] Int. Cl.$^6$ ............................................ C07C 403/00
[52] U.S. Cl. ............................................... 585/351
[58] Field of Search ................................... 585/351

[56] References Cited

U.S. PATENT DOCUMENTS

| | | | |
|---|---|---|---|
| 3,347,932 | 10/1996 | Chechak | 585/351 |
| 3,367,985 | 2/1968 | Surmatis | 585/351 |
| 3,466,335 | 9/1969 | Ruegg et al. | 568/9 |
| 5,310,554 | 5/1994 | Haigh . | |

FOREIGN PATENT DOCUMENTS

| | | |
|---|---|---|
| 0 659 739 | 6/1995 | European Pat. Off. . |
| 2 367 771 | 5/1978 | France . |

OTHER PUBLICATIONS

Pure & Appl. Chem., vol. 63, No. 1, pp. 35–44, 1991, Kurt Bernhard, et al., "Recent Advances in the Synthesis of Achiral Carotenoids" (No Month).

Letters to Nature, vol. 355, pp. 359–361, Jan. 23, 1992, Arthur A. Levin, et al., "9–Cis Retinoic Acid Stereoisomer Binds and Activates the Nuclear Receptor RXRα".

Angew. Chem., vol. 77, pp. 277–360, 1965, H. Freyschlag, et al., "Bildung und Zerfall von Phosphoniumsalzen in der Vitamin–A–Reihe" (No Month).

"Organic Chemistry", Carey, pp. 668–672, 1987.

"Advanced Organic Chemistry", Carey et al. pp. 95–103, 1990.

*Primary Examiner*—Walter D. Griffin
*Assistant Examiner*—Nadine Preisch
*Attorney, Agent, or Firm*—Oblon, Spivak, McClelland, Maier & Neustadt, P.C.

[57] ABSTRACT

β-Carotene products with a high proportion of the 9(Z) isomer are prepared starting from mother liquors from the industrial preparation of β-ionylideneethyltriarylphosphonium salts ($C_{15}$-triarylphosphonium salts) by Wittig reaction of a $C_{15}$-triarylphosphonium salt which has been enriched in the 9Z isomer directly with β-apo-12'-carotenal or else with 2,7-dimethyl-2,4,6-octatrienedial and subsequently with the $C_{15}$-triarylphosphonium salt and subsequent thermal isomerization.

14 Claims, No Drawings

PREPARATION OF β-CAROTENE PRODUCTS WITH A HIGH 9 (Z) CONTENT

The present invention relates to a process for preparing β-carotene products with a high proportion of the 9(Z) isomer starting from mother liquors from the industrial preparation of βion-ylideneethyltriarylphosphonium salts (C₁₅-triarylphosphonium salts) by Wittig reaction of a C₁₅-triarylphosphonium salt which has been enriched in the 9Z isomer directly with β-apo-12'-carotenal or else with 2,7-dimethyl-2,4,6-octatrienedial and subsequently with the C₁₅-triarylphosphonium salt with the (E) configuration.

9(Z)-β-Carotene of the formula I occurs naturally. U.S. Pat. No. 5,310,554 discloses that Dunaliella algae sometimes produce on exposure to intense sunlight more 9(Z)-β-carotene than all-(E)-β-carotene. U.S. Pat. No. 5,310,554 ascribes advantages to 9(Z)-β-carotene in respect of formulation and bioavailability compared with the all-(E) form. In addition, according to statements in Nature 355 (1992) 359–61 and Archives of Biochemistry and Biophysics, 313 (1994) 150–55, 9(Z)-β-carotene is to be regarded as precursor of 9(Z)-retinoic acid which activates the RXRα cell receptor and thus controls embryonic development and cell differentiation and proliferation.

The isolation of products containing 9(Z)-β-carotene from biological material is very elaborate and includes the removal of other lipophilic substances. The object therefore was to prepare corresponding products by chemical means in an extremely simple way.

In the preparation of the C₁₅-triarylphosphonium salt required for industrial vitamin A syntheses and for preparing other vitamin A derivatives, such as retinal and retinoic acid, (see, for example, H. Pommer et al. in Angew. Chem. 77 (1965) 277–360), removal of the required product results in a mother liquor which, besides all-(E)-C₁₅-triphenylphosphonium salt, contains the 9(Z) isomer in a proportion of from 10 to 60% by weight, in particular 30 to 40% by weight, based on total C₁₅-triarylphosphonium salt. Direct use of this mother liquor for preparing β-carotene products with a high content of (Z) isomer is not possible without difficulty.

It is an object of the present invention to develop a process with the aid of which it is possible to prepare the required β-carotene products from these mother liquors from the production of C₁₅-triphenylphosphonium salts and, very generally, from mother liquors from the production of C₁₅-triarylphosphonium salts.

We have found that this object is achieved by a process for preparing β-carotene products with a high content of 9(Z)-β-carotene of the formula I

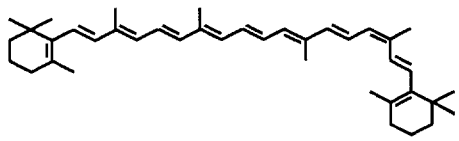

starting from mother liquors from the industrial preparation of β-ionylideneethyltriarylphosphonium salts (C₁₅-triarylphosphonium salts), which comprises A. the proportion of 9(Z)-C₁₅-triarylphosphonium salts in the C₁₅-triarylphosphonium salts isolated from the mother liquors by extraction with water and concentration of the aqueous phase being increased by dissolving the oily C₁₅-triarylphosphonium salt mixture in a lower alkanol and removing the all-(E)-C₁₅-triarylphosphonium salt which crystallizes out on cooling, B. the resulting C₁₅-triarylphosphonium salt which is enriched in the 9(Z)-isomer of the general formula II

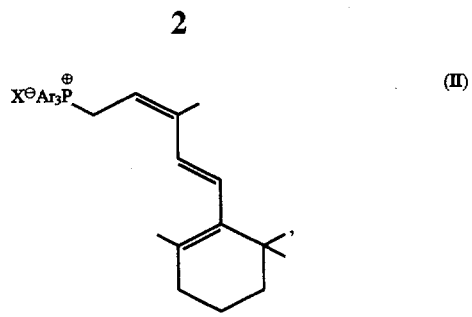

where X is halogen or $HSO_4^-$ and Ar is unsubstituted or substituted phenyl being reacted in the presence of a base in a solvent suitable for Wittig reactions a) either directly with all-(E)-β-apo-12'-carotenal of the formula III

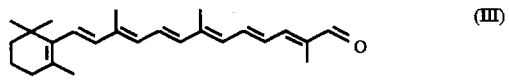

or else b) in the first place with the symmetrical C₁₀-dialdehyde of the formula IV

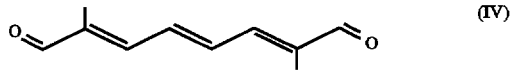

and then the resulting 9(Z)-β-apo-12'-carotenal of the formula V

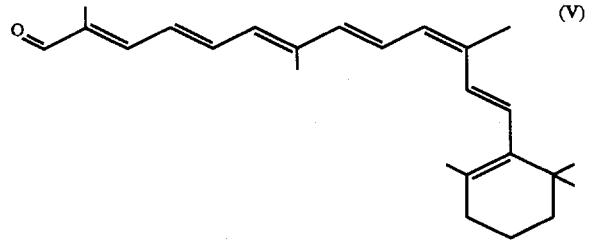

being reacted in the presence of a base in a solvent suitable for Wittig reactions with a 9-(E)-β-ionylidene-ethyltriarylphosphonium salt of the general formula VI

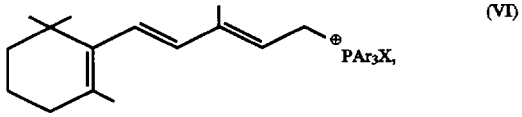

where $X^\ominus$ and Ar have the abovementioned meanings, and

C. if required the resulting β-carotene which has been isolated in a conventional way being subjected to a heat treatment to isomerize the double bond with the (Z) configuration which is formed in the 11 or 11' position of β-carotene.

The process according to the invention is particularly advantageous when the proportion of 9(Z)-C₁₅-triarylphosphonium salt from the mother liquor of the C₁₅-triarylphosphonium salt preparation is increased in step A by a) adding water to the mother liquor and removing the organic phase, b) concentrating the aqueous phase under mild conditions while changing the solvent from water to isopropanol, and c) removing the all-(E)-C₁₅-triarylphosphonium salt which crystallizes out on cooling.

$C_{15}$-Triarylphosphonium salts are prepared in a conventional way generally in aromatic hydrocarbons such as toluene or xylene, in chlorinated hydrocarbons Such as methylene chloride or in lower alkanols such as methanol or isopropanol, in acetonitrile or else in mixtures of these solvents.

Accordingly, the mother liquors used for the process according to the invention consist of one of these solvents or a mixture of solvents, of 9(E)- and 9(Z)-$C_{15}$-triarylphosphonium salt and by-products such as traces of acids, water of reaction and $C_{15}$-hydrocarbon, of triphenylphosphine oxide, and triarylphosphonium salts of the hydrohalic acid or sulfuric acid.

They contain, depending on the reaction conditions, a proportion of from 10 to 60%, preferably 30 to 40%, of the 9(Z) isomer based on the total amount of $C_{15}$-triarylphosphonium salt. The $C_{15}$-triarylphosphonium salts are extracted from this mother liquor with water, and the aqueous phase is concentrated under mild conditions. The resulting oil is taken up in a sufficient quantity of a lower alkanol, preferably isopropanol, for the concentration of the salt to be from 30 to 70% by weight, preferably 40 to 60% by weight, in particular 45 to 55% by weight. The resulting solution is then left to stand from $-50°$ to $25°$ C., preferably $-30°$ to $0°$ C., during which all-(E)-$C_{15}$-triarylphosphonium salt crystallizes out and can thus be removed. After this enrichment of the 9(Z)-$C_{15}$-salt the ratio of 9(Z)- to all-(E)-$C_{15}$-triphenylphosphonium salt in the mother liquor is from about 1:1 to 50:1. In the example, a ratio of 90:6, equivalent to about 15:1, was achieved.

Further enrichment of the 9(Z) isomer is possible on the basis of kinetic control of the subsequent Wittig reaction, because the remaining all-(E) isomer undergoes the Wittig reaction very much more quickly than the 9(Z)-$C_{15}$-triarylphosphonium salt. This is because reaction of the $C_{15}$-triarylphosphonium salt mixture in a Wittig reaction with an aldehyde, for example acetaldehyde, in an amount corresponding to the proportion of all-(E)-$C_{15}$ salt still present, and acid workup of the reaction mixture permits pure 9(Z)-$C_{15}$-triarylphosphonium salt to be isolated because of the kinetic differentiation.

Linkage of the $C_{15}$-triarylphosphonium salt enriched in the 9(Z) isomer of the general formula II to all-(E)-β-apo-12'-carotenal of the formula III in stage Ba), and linkage thereof to the C10-dialdehyde of the formula IV to give 9(Z)-β-apo-12'-carotenal of the formula V in stage Bb), and further Linkage of the 9(Z)-β-apo-12'-carotenal obtained in stage Bb) to the all-(E)-triarylphosphonium salts of the general formula VI generally take place under the conditions customary in polyene chemistry for Wittig reactions. Reference may be made to DE 10 68 703 or DE 10 68 705 for details of the general conditions for Wittig reactions.

The bases generally used for the Wittig reaction are alkali metal hydroxides, alkaline earth metal hydroxides, amines, ammonia or alkali metal carbonates.

Weak bases such as organic amines, ammonia, alkali metal carbon- ates or magnesium hydroxide, but also alkali alcoholates, are particularly advantageously used.

The reaction is generally carried out at from $-20°$ C. to $50°$ C., preferably from $0°$ C. to $20°$ C.

Suitable solvents are those which are inert under the reaction conditions and dissolve the precursors to a sufficient extent. For example, it is advisable to react that sparingly soluble dialdehyde of the formula IV in the presence of methylene chloride or dimethylformamide. The reaction medium can be in the form of a homogeneous phase or two phases. Thus, for example, pure methylene chloride, pure dimethylformamide, lower alkanols or mixtures of these solvents can be used. However, it is also possible to use two-phase systems such as methylene chloride/water or heptane/water. The process according to the invention can moreover be carried out either by introducing both starting compounds into the solvent and adding the base, or else making a solution of the $C_{15}$-triarylphosphonium salt, adding the base and only then adding a solution of the appropriate aldehyde. The mixtures are worked up, for example, by taking up the required product in heptane and removing triarylphosphine oxide using water/methanol mixtures. Residues of β-apo-12'-carotenals used can, if required, be removed by filtration through silica gel.

Particularly high proportions of 9(Z) isomer are obtained in the process according to the invention when the resulting β-carotene which has been isolated in a conventional way is, in stage C, heated at from $70°$ to $80°$ C. in inert hydrocarbons or alkanols, preferably in heptane or isobutanol, for about 1 to 2 hours to isomerize the double bond with the (Z) configuration in the 11 or 11' position of the β-carotene formed, and/or when the crude β-apo-12'-carotenal of the formula V initially obtained in stage Bb) and isolated in a conventional way is heated at from $70°$ C. to $80°$ C. in inert hydrocarbons or alkanols, preferably in heptane or isobutanol, for about 1 to 2 hours to isomerize the double bond with the (Z) configuration in the 11 position of the 9(Z), 11(Z) isomer formed as byproduct.

Using the process according to the invention it is possible in a relatively simple way to obtain β-carotene products with proportions of 9(Z) of about 60–80% (HPLC % areas). About 10% comprise all-(E)-β-carotene, and the remainder is other (Z) compounds and isomers with two double bonds with the (Z) configuration.

The following examples are intended to illustrate the process according to the invention.

EXAMPLE 1

A. Enrichment of 9 (Z)-$C_{15}$-triphenylphosphonium salt 4.8 liters of a mother liquor from the industrial preparation of 3-methyl-5-(2,6,6-trimethyl-1-cyclohexenyl)-2,4-pentadie-nyltriphenylphosphonium bisulfate ($C_{15}$-triphenylphosphonium sulfate) in heptane/isopropanol were vigorously mixed with 480 ml of water. After removal of the organic phase, the aqueous solution was completely evaporated in a rotary evaporator at $70°$ C. adding about 3 liters of isopropanol in portions, initially for removal of the water under milder conditions and finally to precipitate 9(E)-$C_{15}$-triphenylphosphonium bisulfate.

523 g of an approximately 50% by weight solution of $C_{15}$-triphenylphosphonium bisulfate were obtained, and HPLC analysis showed that the 9(Z) isomer predominated in the ratio of 1.5:1.

The solution was subsequently seeded with 9(E)-$C_{15}$-triphenyl-phosphonium bisulfate and left to stand at $5°$ C. for 16 hours, and then the crystallized 9(E)-$C_{15}$ salt was filtered off. The remaining 336 g of mother liquor contained about 2% water and the $C_{15}$-triphenylphosphonium bisulfate in a ratio of 8.4:1 and can be stored at $5°$ C. with negligible decomposition.

B. Wittig reaction with β-apo-12'-carotenal 56.3 g (0.31 mol) of a 30% by weight methanolic solution of sodium methoxide were added dropwise to a mixture of about 120 g (about 1 mol) of the $C_{15}$-triphenylphosphonium bisulfate solution prepared as in Example 1A; 158 ml of water, 180 ml of n-hexane and 36 g (0.1 mol) of β-apo-12'-carotenal ($C_{25}$-Al) at $20°$ C. The mixture was then stirred at 50° C. for 1 hour, 240 ml of methanol were added, and the lower phase was removed. The heptane was washed at 50° C. with 110 ml of 60% by weight aqueous methanol and concentrated in a rotary evaporator. 61 g of a crude product were obtained, and the $C_{25}$-Al still present therein was removed by filtration through silica gel and washing with cyclohexane/diisopropyl ether (9:1). Evaporation of the filtrate containing β-carotene in a rotary evaporator resulted in 48.1 g (corresponding to 86.1% of theory) of a β-carotene isomer mixture which had the following composition according to HPLC:

1.4% 13(Z)-β-carotene, 54.6% 9(Z)-β-carotene, 11% all-(E)-β-carotene, 33% 9(Z), 1(Z)-β-carotene and other isomers.

C. Isomerization

A solution of the β-carotene isomer mixture prepared as in Example 1B in 400 ml of n-hexane was refluxed at about 70° C. for 2 hours and then concentrated in a rotary evaporator. The β-carotene isomer mixture which resulted as a viscous oil had the following composition according to HPLC:

2.6% 13(Z)-β-carotene, 68.9% 9(Z)-β-carotene, 11.3% all-(E)-β-carotene and 17.2% other isomers.

EXAMPLE 2

A two-phase mixture consisting of 120 g (about 0.1 mol) of the 9(Z)-$C_{15}$-triphenylphosphonium salt solution prepared as in Example 1A and a solution of 18 g (0.11 mol) of 2,6-di-methyl-2,4,6-octatrienedial in 220 ml of dichloromethane was saturated with ammonia gas at about 30° C. The phases were then separated, the dichloromethane phase was concentrated in a rotary evaporator, and the resulting residue was dissolved in a mixture of 150 ml of heptane and 100 ml of methanol at 50° C. After adding 65 ml of water, the lower phase was removed. The upper phase contained, according to HPLC analysis, an (E,Z) mixture of β-apo-12'-carotenal containing about 56% 9(Z)- and about 30% (9Z, 11Z)-β-apo-12'-carotenal.

The heptane phase was then mixed with a Solution of 62 g of approximately 90% pure β-ionylideneethyltriphenylphosphonium bisulfate in 100 ml of methanol and then, at about 30° C., 45.5 g (0.25 mol) of a 30% by weight methanolic sodium methoxide solution were added dropwise.

After 30 min, 120 ml of water Were added, the lower phase was separated off at 50° C., and the upper phase was washed twice with 120 ml of 60% aqueous methanol each time. The heptane phase was concentrated in a rotary evaporator (bath at 50° C., 50 mbar) to afford 61.5 g of (E,Z)-β-carotene.

The crude product was purified by filtration through silica gel as described in Example 1, taken up in 200 ml of heptane and thermally isomerized (1 h at 80° C.) to convert double bonds with the (11Z) and (11'Z) configuration into the E form. Concentration in a rotary evaporator resulted in β-carotene as a viscous oil with the following composition according to HPLC analysis: 4.4% 13(Z)-β-carotene, 66% 9(Z)-β-carotene, 9.6% all-(E)-β-carotene and about 20% other isomers of β-carotene.

We claim:

1. A process for preparing β-carotene products with a high content of 9(Z)-β-carotene of formula I:

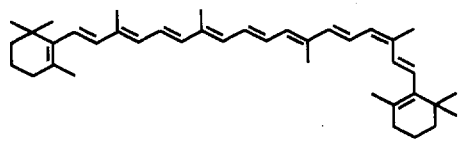

from a mother liquor from the industrial preparation of $C_{15}$-triarylphosphonium salts, comprising:

(a) extracting a mother liquor comprising a 9(Z)-$C_{15}$-triarylphosphonium salt of formula (II) and an all-(E)-$C_{15}$-triarylphosphonium salt of formula (VI):

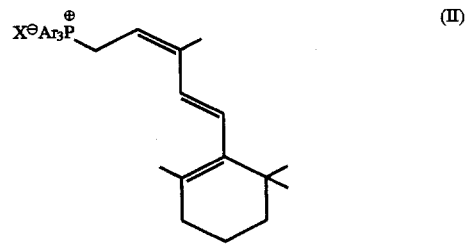

with water to produce an aqueous solution containing the salts, wherein X is halogen or $HSO_4$ and Ar is an unsubstituted or substituted phenyl group;

(b) precipitating the all-(E)-$C_{15}$-triarylphosphonium salt of formula (VI) by either (1) concentrating the aqueous solution containing the salts to produce the salts as an oil, followed by dissolving the oil in a lower alkanol, or (2) concentrating the aqueous solution containing the salts while changing the solvent from water to a lower alkanol;

(c) removing the precipitated all-(E)-$C_{15}$-triarylphosphonium salt to produce a $C_{15}$-triarylphosphonium salt enriched in the 9(Z)-isomer of formula (II);

(d) reacting the $C_{15}$-triarylphosphonium salt enriched in the 9(Z)-isomer of formula (II) in the presence of a base in a solvent suitable for a Wittig reaction with either (1) all-(E)-β-apo-12'-carotenal of formula (III):

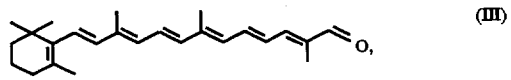

or (2) a symmetrical $C_{10}$-dialdehyde of formula (IV):

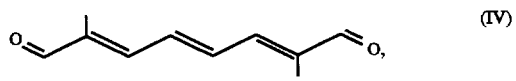

followed by reacting the resulting 9(Z)-β-apo-12'-carotenal of formula (V):

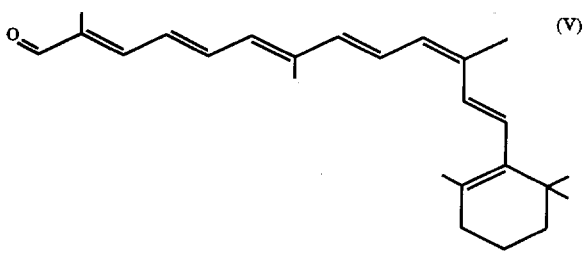

(V)

in the presence of a base in a solvent suitable for a Wittig reaction with said all-(E)-β-C₁₅-triarylphosphonium salt of formula (VI), to produce a β-carotene product enriched in the 9(Z) isomer; and (e) optionally, isomerizing the (Z) double bond at the 11 or 11' position of the β-carotene product by heating.

2. A process as claimed in claim 1, wherein the lower alkanol in step (b) is isopropanol.

3. A process as claimed in claim 1, wherein the concentration of said C₁₅-triarylphosphonium salts in the lower alkanol is 30 to 70% by weight.

4. A process as claimed in claim 1, wherein the concentration of the C₁₅-triarylphosphonium salts in the lower alkanol is 40 to 60% by weight.

5. A process as claimed in claim 1, wherein the concentration of the C₁₅-triarylphosphonium salts in said lower alkanol is 45 to 55% by weight.

6. A process as claimed in claim 1, wherein the ratio of the 9(Z)-C₁₅-triarylphosphonium salt of formula (II) to the all-(E)-C₁₅-triarylphosphonium salt of formula (VI) after removing the precipitated all-(E)-C₁₅-triarylphosphonium salt is 1:1 to 50:1.

7. A process as claimed in claim 1, comprising step (e).

8. A process as claimed in claim 7, wherein step (e) is conducted in an inert solvent at a temperature of 70° to 80° C. for about 1 to 2 hours.

9. A process as claimed in claim 8, wherein the inert solvent is heptane or isobutanol.

10. A process as claimed in claim 1, wherein said base is selected from the group consisting of an organic amine, ammonia and an alkali metal alcoholate.

11. A process as claimed in claim 1, further comprising isomerizing the 9(Z)-β-apo-12'-carotenal of formula (V) containing an 11(Z) double bond by heating at a temperature of 70° to 80° C. in an insert solvent for 1 to 2 hours.

12. A process as claimed in claim 11, wherein said inert solvent is heptane or isobutanol.

13. A process as claimed in claim 1, wherein step (b) comprises concentrating the aqueous solution containing the salts to produce the salts as an oil, followed by dissolving the oil in a lower alkanol.

14. A process as claimed in claim 1, wherein step (b) comprises concentrating the aqueous solution containing the salts while changing the solvent from water to a lower alkanol.

* * * * *